United States Patent
Dworschak et al.

(10) Patent No.: US 11,364,108 B2
(45) Date of Patent: Jun. 21, 2022

(54) INTRAOCULAR LENS FOR IMPLANTATION IN A CILIARY SULCUS OF AN EYE

(71) Applicant: Investmed Kft., Zsambek (HU)

(72) Inventors: Rudiger Dworschak, Deidesheim (DE); Laszlo Kontur, Munich (DE)

(73) Assignee: INVESTMED KFT.

(*) Notice: Subject to any disclaimer, the term of this patent is extended or adjusted under 35 U.S.C. 154(b) by 114 days.

(21) Appl. No.: 16/399,210

(22) Filed: Apr. 30, 2019

(65) Prior Publication Data

US 2019/0254809 A1 Aug. 22, 2019

Related U.S. Application Data

(63) Continuation-in-part of application No. 13/609,339, filed on Sep. 11, 2012, now abandoned.

(30) Foreign Application Priority Data

Sep. 14, 2011 (FR) ...................................... 1158196

(51) Int. Cl.
*A61F 2/16* (2006.01)

(52) U.S. Cl.
CPC ............ *A61F 2/1613* (2013.01); *A61F 2/161* (2015.04); *A61F 2/1645* (2015.04); *A61F 2/1694* (2013.01); *A61F 2002/1681* (2013.01)

(58) Field of Classification Search
None
See application file for complete search history.

(56) References Cited

U.S. PATENT DOCUMENTS

| | | | | |
|---|---|---|---|---|
| 5,476,512 | A * | 12/1995 | Sarfarazi | A61F 2/16 623/6.39 |
| 5,693,094 | A * | 12/1997 | Young | A61F 2/1613 128/898 |
| 5,800,532 | A * | 9/1998 | Lieberman | A61F 2/1618 351/159.08 |
| 6,461,384 | B1 * | 10/2002 | Hoffmann | A61F 2/1616 623/6.51 |
| 6,749,633 | B1 * | 6/2004 | Lorenzo | A61F 2/161 623/6.36 |
| 2002/0072795 | A1 * | 6/2002 | Green | B29D 11/023 623/6.34 |
| 2002/0072796 | A1 * | 6/2002 | Hoffmann | A61F 2/1608 623/6.43 |
| 2005/0246017 | A1 * | 11/2005 | Messner | A61F 2/1608 623/6.16 |

(Continued)

*Primary Examiner* — Leslie Lopez
(74) *Attorney, Agent, or Firm* — Olson & Cepuritis, Ltd.

(57) ABSTRACT

A foldable intraocular lens, made from a foldable soft material, for implantation in a ciliary sulcus of an eye having an iris, is provided with an optically active lens part having an optical axis and at least four haptics unitary with the optically active lens part and uniformly spaced about a periphery of the optically active lens part.
The optically active lens part having a non-convex rim between any two neighboring haptics being free from surface irregularities that interfere with the iris.
Each haptic comprising a closed loop, and a shoulder connecting the loop with the optically active lens part, the haptic loops being elastically deformable in a plane perpendicular to the optical axis of the optically active lens part in a direction toward the optically active lens part.

17 Claims, 5 Drawing Sheets

(56) References Cited

U.S. PATENT DOCUMENTS

2006/0142855 A1* 6/2006 Vaudant .................... A61F 2/16
 623/6.16
2010/0106245 A1* 4/2010 Rombach .............. A61F 2/1613
 623/6.39

* cited by examiner

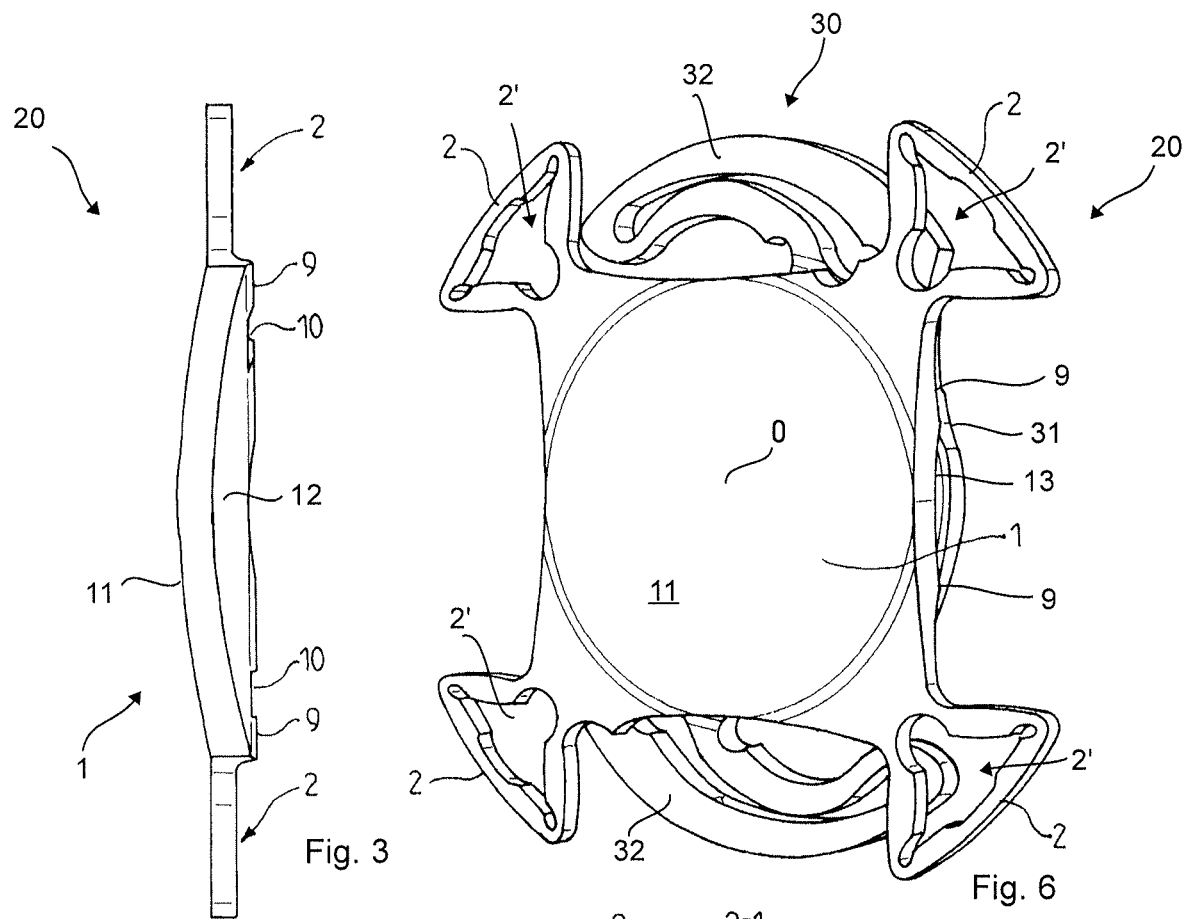
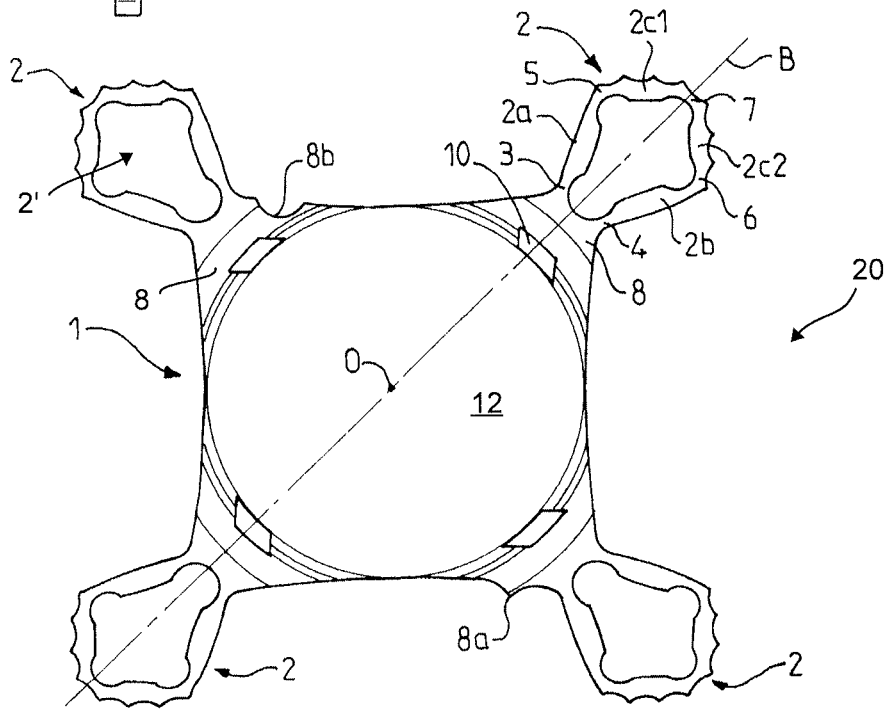
Fig. 3
Fig. 6
Fig. 7

INTRAOCULAR LENS FOR IMPLANTATION IN A CILIARY SULCUS OF AN EYE

CROSS-REFERENCE TO RELATED APPLICATIONS

This application is a continuation-in-part of U.S. patent application Ser. No. 13/609,339, filed on Sep. 11, 2012, which claims priority of French Application No. 1158196, filed on Sep. 14, 2011, each of which is incorporated herein in its entirety.

TECHNICAL FIELD

The invention relates to lenses implantable in the eye and generally called intraocular lenses (IOL). It relates more particularly to lenses for implantation in the ciliary sulcus, between the iris and the capsular bag, both when the latter, after ablation of the crystalline lens, is unable to receive a corrective lens, and also when said capsular bag already contains an intraocular lens, the sulcus lens then being intended to correct the residual or resulting deficiencies after the implantation of a main lens in the capsular bag, or else when it is necessary to add new features to the optical system of the eye, such as:
  correction of corneal astigmatism,
  modification of near sight by means of multifocal lenses,
  fitting of a filter for blue light in cases of sensitivity to light.

BACKGROUND

If the intraocular lens already implanted within the capsular bag is to be retained then any corrective additional intraocular lens needs to be positioned anterior to the capsular bag, hence either in the anterior chamber of the eye or in the posterior chamber, between the pupil and the capsular bag, in the ciliary sulcus. Implanting an intraocular lens in the anterior chamber is not recommended in case of patients who have glaucoma, a shallow anterior chamber, insufficient iris tissue, or corneal endothelial dystrophy. Ciliary sulcus implantation can also cause severe complications as prior art IOLs are prone to so-called pupillary capture (or iris capture) when implanted in the ciliary sulcus. Pupillary capture is defined as dislocation or entrapment of all or part of an IOL optic through the pupillary aperture. Postoperative pupillary capture of the IOL optic can occur for a variety of reasons like improper placement of the IOL haptics, shallowing of the anterior chamber, or anterior displacement of the posterior chamber IOL optic, and it is much more common in case of ciliary sulcus IOLs than capsular bag IOLs due to the proximity of the pupil.

Pupillary capture can cause problems with glare, photophobia, chronic uveitis, unintended myopia, or even monocular diplopia as well as excessive pain in extreme cases. Mydriatics can sometimes be used successfully to free the iris through pharmacologic manipulation of the pupil. If conservative management fails, surgical intervention may be required to free the iris or reposition the IOL.

It is an objective of the present invention to provide a simple, cheap and safe intraocular lens that can be implanted in the ciliary sulcus without the risk of causing pupillary capture.

A further disadvantage of the known sulcus lenses is that they have a natural tendency to turn and to move off centre as a result of the very irregular anatomical structure of the ciliary sulcus and the instability of the movements of the latter.

The invention further aims to overcome this disadvantage and to make available intraocular sulcus lenses of which the haptics ensure a perfect hold of the optical part, regardless of the anatomical structure of the sulcus of the eye of the patient in whom they are implanted, and which do not pose the risk of rotation and off-centering of the known sulcus lenses.

SUMMARY

The inventors have realized that with appropriate design of the IOL optic and the IOL haptics it is possible to prevent pupillary capture of an IOL implanted in the ciliary sulcus.

Accordingly, the invention relates to an intraocular lens, IOL, that is made from a foldable soft material like acrylate or silicone. The IOL is designed to be surgically implanted into the ciliary sulcus of an eye.

The foldable IOL comprises an optically active lens part and at least four unitary haptics spaced about a periphery of the optically active lens part for fixing and stabilizing the IOL within the ciliary sulcus of the patient's eye. The rim of the optically active lens part is non-convex (concave or straight) between any two neighboring haptics in order to prevent iris capture, which is a common problem associated with prior art sulcus lenses. In the context of the present invention the rim of the optically active lens part is understood to be non-convex (concave or straight) between any two neighboring haptics if the orthogonal projection of the IOL on to a plane perpendicular to the optical axis of the optically active lens part is substantially a concave or straight line viewed from the optical axis. The rim of the optically active lens part may have local surface irregularities, such as projections or recesses, however, the rim is free from any surface irregularities (projections and/or recesses) that interfere with the iris of the eye in order to prevent iris capture. Preferably the non-convex rim is free from any surface irregularities, such as projections or recesses, that have a radius greater than 0.6 mm, more preferably greater than 0.3 mm.

According to a preferred embodiment each haptic loop comprises an elongated arched upper segment with opposed end portions and a pair of lower segments, each lower segment pivotably joined to the upper segment at one of said end portions of the upper segment and to the shoulder at a distance therebetween, such that said lower segments converge in the direction of the optically active lens part and the length of each upper segment is less than the sum of the lengths of said lower segments and said distance.

Such a design has for effect that under the compression forces exerted by the structures of the eye in the direction of the optical part, the haptics cannot deform beyond the point of maximum extension in which the arched upper segments are flattened. This provides great flexibility of the upper part of the haptics in contact with the ciliary sulcus while at the same time limiting the deformation to a minimum target diameter, preferably of between 10.5 mm and 12.5 mm. The haptic loops are preferably spaced symmetrically, more preferably uniformly about the periphery of the optically active lens part, which in combination with their deformability, eliminates the risk of undesirable rotation of the lens under the effect of the forces exerted thereon (contraction of the internal structures of the eye, movements of the eye, rubbing exerted on the eye).

Further advantageous embodiments of the invention are defined in the attached dependent claims.

BRIEF DESCRIPTION OF THE DRAWINGS

Further details of the invention will be apparent from the accompanying figures and exemplary embodiments.

FIG. 3 is a schematic sectional view in the median plane of the IOL shown in FIG. 1.

FIG. 6 is a schematic back view of another preferred embodiment of a IOL according to the invention showing a non-deformed state of four haptic loops with solid line and illustrating a deformed state of the haptic loops with dashed line.

FIG. 7 is an enlarged schematic view of one haptic loop according to FIG. 6 showing the non-deformed state with solid line and the deformed state with dashed line.

DETAILED DESCRIPTION

Figure 2:
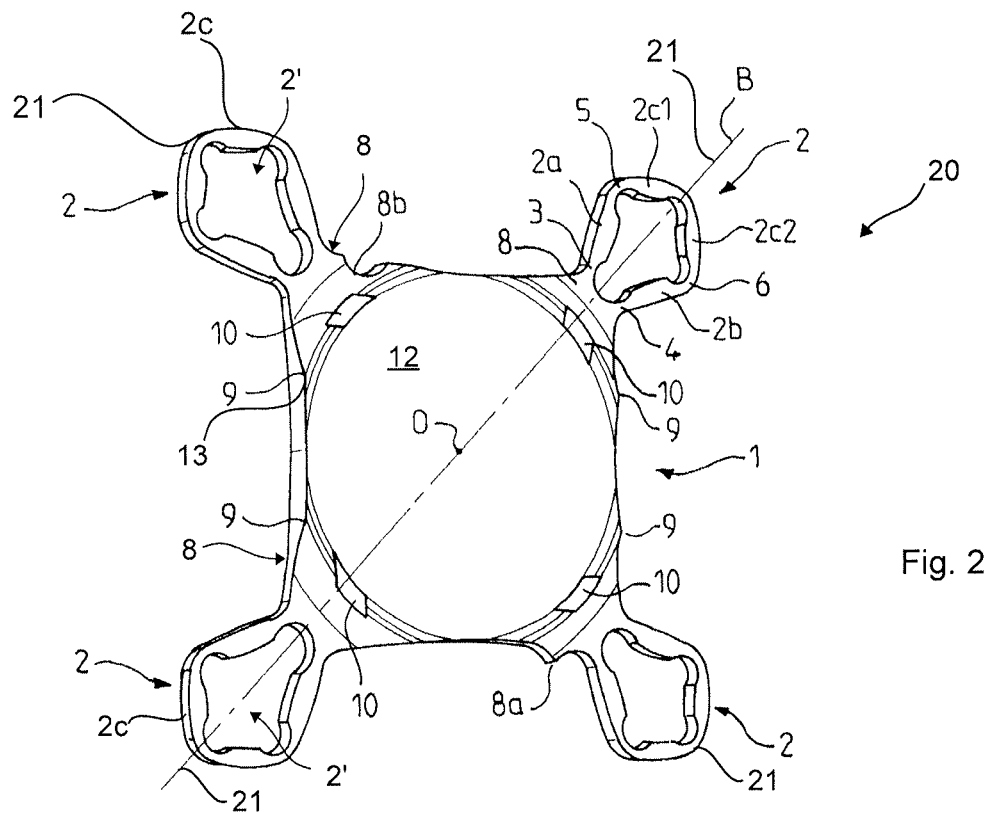
FIG. 2 is a schematic perspective back view of the IOL.
Figure 1:
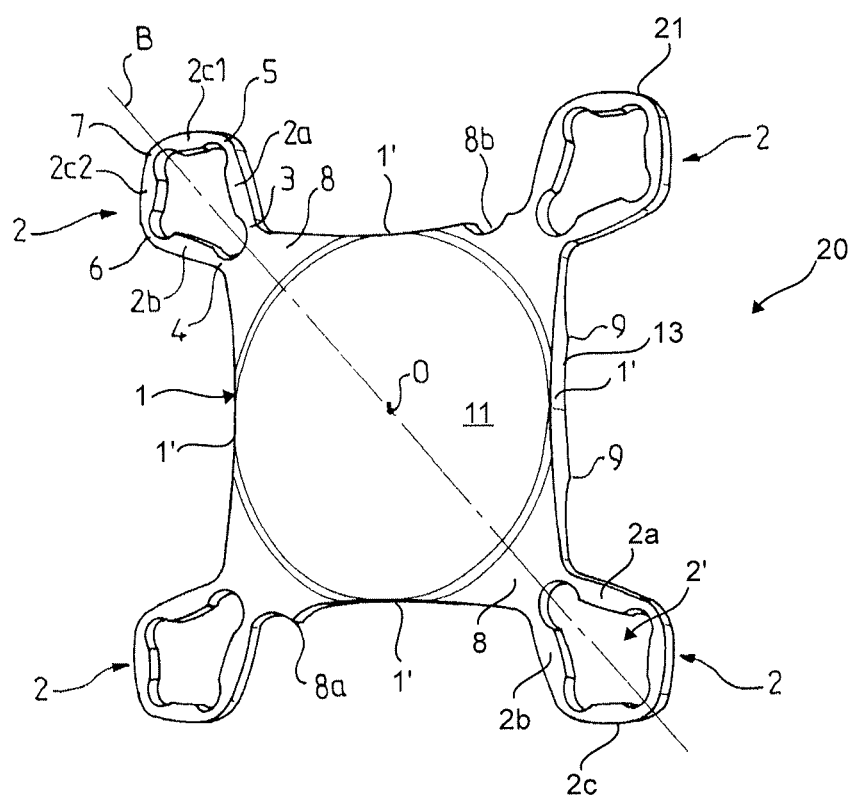
FIG. 1 is a schematic perspective front view of a preferred embodiment of a IOL according to the invention.

FIGS. 1-3 schematically illustrate a first preferred embodiment of the secondary intraocular lens, IOL, 20 according to the invention for implantation in a ciliary sulcus of an eye. The IOL 20 is made from a foldable soft material such as acrylate or silicone. According to the present embodiment the IOL 20 comprises an optically active lens part 1 and four haptics 2, formed with loops 2a, unitary with the optically active lens part 1 and uniformly spaced about a periphery of the optically active lens part 1 for fixing and stabilizing the IOL 20 within a patient's eye and. FIG. 1 shows an anterior face 11 of the active lens part 1 and FIG. 2 shows a posterior face 12 of the active lens part 1.

The optically active lens part 1 preferably has a diameter between 4 and 10 mm, more preferably between 5 and 7 mm.

Figure 10:
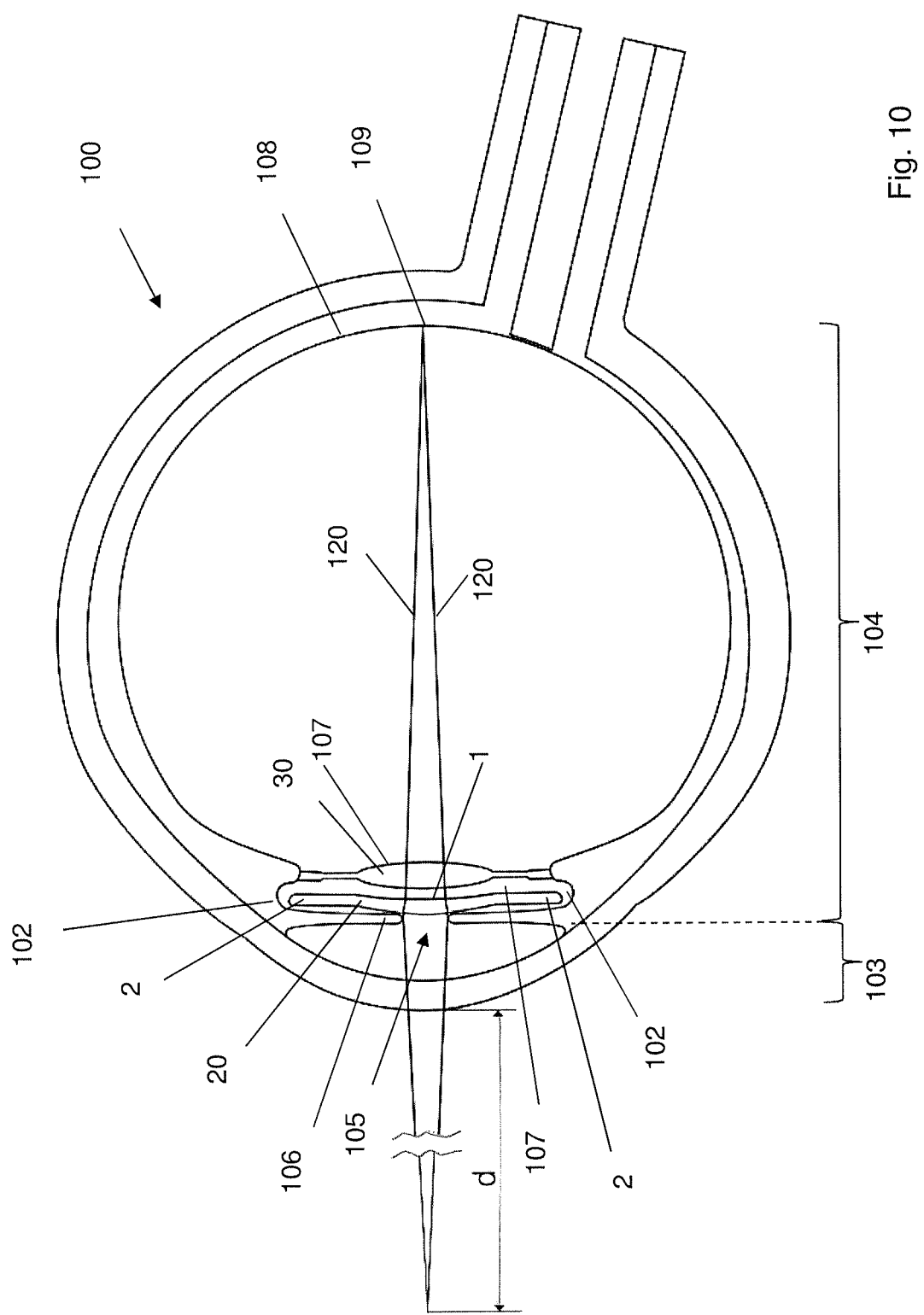
FIG. 10 is a schematic cross-sectional view of the IOL and the primary IOL implanted in an eye and illustrating light rays passing through the two lenses during near vision.

The IOL 20 according to the present invention is intended to be surgically implanted into a ciliary sulcus 102 of an eye 100 possibly as a secondary IOL 20, which is implanted in an anterior position with respect to a primary IOL 30 already implanted in the patient's eye 100 as illustrated in FIG. 10. The eye 100 is divided into an anterior chamber 103 and a posterior chamber 104 by a pupil 105 which is formed by the iris 106 of the eye 100. The ciliary sulcus 102 lies in the posterior chamber 104 between the iris 106 and a capsular bag 107, which contains the natural lens of the eye 100. In case of a pseudophakic eye 100 the natural crystalline lens has been removed and replaced by the primary IOL 30, which is generally implanted within the capsular bag 107.

Because the IOL 20 lies adjacent the pupil 105 when implanted in the ciliary sulcus 102 it is prone to pupillary capture. Pupillary capture occurs when part of the pupil's 105 margin, the iris 106 is displaced posteriorly behind the IOL optic, which then appears to lie in the anterior chamber 104 of the eye 100. In order to prevent pupillary capture, the IOL 20 according to the present invention has four haptic loops 2' and a rim 1' of the optically active lens part 1 is non-convex (concave and/or straight) between any two neighboring haptic loops 2. The rim 1' of the optically active lens part 1 may, however, have minor projections or recesses (e.g. for the purpose of positioning) which are small enough (preferably smaller than 1.5 mm, more preferably smaller than 0.6 mm, most preferably smaller than 0.3 mm) not to interfere with the iris 106, i.e. small enough for the iris 106 not to be captured thereon or therein, respectively.

Pupillary capture is preferably further prevented by providing each haptic 2 with a flat, thin, generally triangular shoulder 8 forming a transition between the optically active lens part 1 and the haptic loop 2'. The shoulders 8 are of generally triangular shape and have a thickness of about 0.2 mm. The generally triangular shape means that the shoulders 8 narrow in the direction of the haptic loops 2, preferably as a continuation of the concave or straight rim 1' of the optically active part 1 and thereby have the effect of avoiding a risk of the iris 106 being caught by the haptic loops 2'. The shoulders 8 have a cross-section that generally decreases in the direction of the loop 2' extending therefrom. The shoulders 8 may be provided with a lateral projection 8a and/or a recess 8b for performing a positioning function as long as such projection 8a and recess 8b is small enough to prevent the iris 106 to be captured thereon and therein, respectively. Alternatively, such a projection and/or recess may be formed on the rim 1' of the optically active lens part 1.

The design of the haptic loop 2' further contributes to preventing pupillary capture.

The IOL 20 has four haptics 2 regularly distributed around the optically active lens part 1. Since the haptics 2 are identical, the reference numbers have not been placed on all of them, in order not to complicate the drawing.

The haptic loops 2' form two diametrically opposed pairs, one pair being arranged along a median transverse axis B passing through the optical axis O, the other pair being arranged transversal to axis B.

The loops 2' preferably have a symmetric shape the axis of symmetry preferably corresponding to a diameter of the IOL 20 passing through poles 21 of two opposing loops 2'. One such axis of symmetry corresponds to the median transverse axis B indicated in FIGS. 1 and 2. This symmetric haptic shape eliminates any torque acting on the IOL 20 after implantation in the ciliary sulcus 102, whereby the IOL 20 will not be prone to rotation around the optical axis O of the optically active lens part 1 which is important if the optic is designed to have a toric shape in order to correct for astigmatism in a way known in the art.

According to the present embodiment each loop 2' is formed by two lower segments 2a, 2b which, at one end, are connected by two lower elastic flexion points 3, 4 to the shoulder 8 of the haptic 2, and, at the other end, are connected by two upper elastic flexion points 5, 6 to opposed end portions of an upper segment 2c. According to the present embodiment the upper segment 2c comprises two parts 2c1, 2c2, which are joined to each other by a further elastic flexion point 7. The outer edge of the lower segments 2a, 2b of each loop is preferably, generally straight. The elastic flexion points 3, 4, 5, 6, 7 allow for the elastic deformation of the loops 2', other portions of the loop 2' are preferably more ridged in order to ensure that upon compression any flexion of the loops 2' occurs at the flexion points 3, 4, 5, 6, 7.

Figure 5:
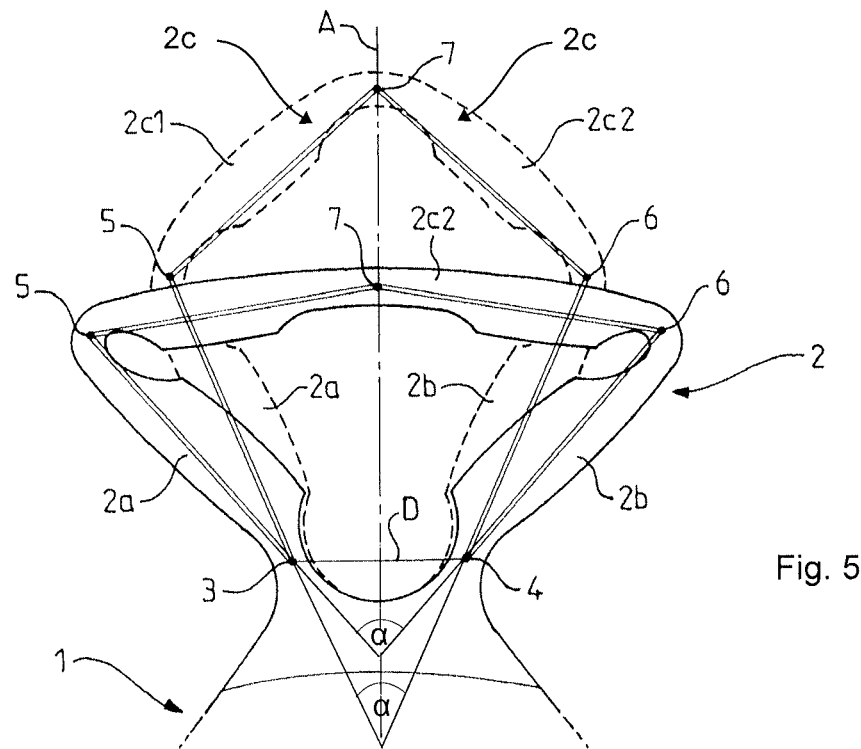
FIG. 5 is an enlarged schematic view of one haptic loop showing the non-deformed state with solid line and the deformed state with dashed line.
Figure 4:
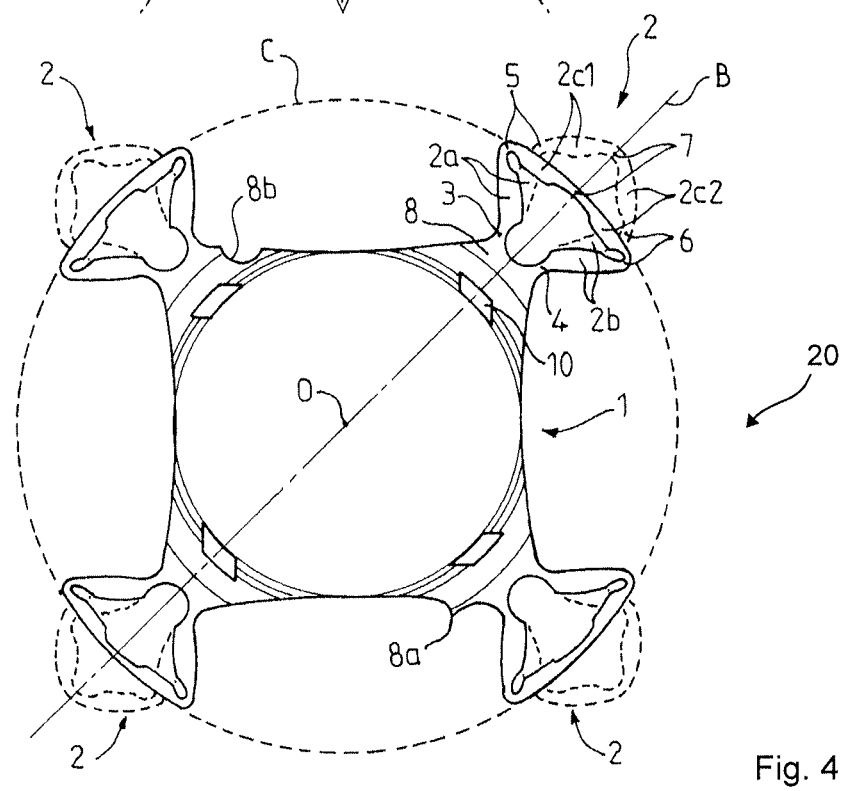
FIG. 4 is a schematic back view of the IOL showing a non-deformed state of four haptic loops with solid line and illustrating a deformed state of the haptic loops with dashed line.

FIG. 4 provides a schematic illustration of the haptic loops 2' according to the invention at a non-deformed rest position (broken lines) and in the state of maximum deformation (solid lines). FIG. 5 is an enlarged view of one loop 2' with a skeleton diagram laid thereover in order to facilitate the understanding of the deformation. The lower flexion points 3, 4 are spaced from each other by a distance D (see FIG. 5), such that they converge in the direction of the optically active lens part 1 and diverge in the direction of the upper segment 2c with respect to the median vertical axis A passing through the pole of a haptic loop 2' and through an optical axis O of the lens. The sum of the lengths of the lower segments 2a, 2b and of the distance D is greater than the length of the upper segment 2c. Under the effect of compression forces acting on the pole of the loop 2', which is substantially at the flexion point 7, in the direction of the optically active lens part 1, the pivoting of the lower segments 2a, 2b in a plane perpendicular to the optical axis O produces the displacement of the upper flexion points 5, 6 in the direction of the optically active lens part 1 and the flattening of the upper segment 2c by pivoting of the upper segment parts 2c1, 2c2 around the upper flexion point 7 as illustrated in FIGS. 4 and 5.

Under the effect of the compression forces exerted on the haptic loops 2', the latter deform with a gradual flattening movement of the upper segments 2c1, 2c2 and spacing-apart of the lower segments 2a, 2b about flexion points 3, 4, 5, 6 and 7. Thus the two lower segments 2a, 2b and the upper segment 2c of each loop 2' are configured to occupy a non-deformed state in which the lower segments 2a, 2b are lying at a first angle to each other and the upper flexion points 5, 6 are at a first distance from each other, and an elastically deformed state in which the arched upper segment 2c flattens, the lower segments 2a, 2b are lying at a second angle to each other and the upper flexion points 5, 6 are at a second distance from each other, the second angle being greater than the first angle and the second distance being greater than the first distance.

The size ratio of the lower segments 2a, 2b with respect to the upper segments 2c1, 2c2, their spacing of distance D from each other and their convergence in the direction of the optically active lens part 1, preferably in the direction of the optical axis O, ensure that the movement of deformation does not go beyond a return point at which the upper segments 2c1, 2c2 are substantially in alignment with each other. Accordingly, by design, the haptic loops 2' cannot continue to deform beyond the lower position shown in FIGS. 4 and 5 with solid line.

In this way a haptic loop 2' is obtained that can deform elastically in the direction of the optically active lens part 1 by a limited distance, this deformation being blocked when a maximum opening angle α of the lower segments 2a, 2b is reached. The maximum opening angle α is preferably between 70° to 170°, more preferably between 70° to 130°. In practice, the loop 2' ceases to deform any further when fully abutting the circular perimeter of the ciliary sulcus 102. The maximum flattening of the upper segments 2c is reached when the outer edge of each upper segment 2c follows the curvature of circle C indicated with a dashed line in FIG. 4. Accordingly, the circle C symbolizes the position of maximum compression of the haptic loops 2. In practice, the dimensions of the IOL 20 are chosen such that the diameter of the circle C will be between 10.5 mm and 12.5 mm, which corresponds to the overall diameter of the IOL 20, in the state of maximum compression of its haptic loops 2'.

The lower segments 2a, 2b preferably have a length of the order of 1.6 mm, and the upper segments 2c1, 2c2 a length of the order of 1.4 mm. The flexion points 3, 4, 5, 6 and 7 are preferably obtained by reducing the cross section of the material from which each haptic loop 2' is made.

The IOL 20 according to the invention can be implanted in the ciliary sulcus 102 as a secondary IOL anterior of a primary IOL 30 implanted in the capsular bag 107. FIG. 6 illustrates the position of the secondary IOL 20 with respect to the primary IOL 30, which generally comprises an optically active lens part 31 and haptics 32. In order to adapt to the anterior face of the primary IOL 30 present in the capsular bag 107 the optically active lens part 1 is preferably concavo-convex as can be best seen in FIG. 3. In order to ensure that a space permitting circulation of the aqueous humor is maintained between the adjacent faces of the optically active lens parts 31 and 1 of the primary IOL 30 and of the secondary IOL 20, respectively, the secondary IOL 20 has four projections or stubs 9 arranged regularly on a posterior edge 13 of a posterior face 12 of the optically active lens part 1. For this same purpose, recesses 10 are additionally arranged along the perimeter of the posterior face 12 of the optically active lens part 1 and substantially centered on the diameters passing through the poles of the haptic loops 2.

FIG. 7 illustrates a modified embodiment of the IOL 20 according to FIGS. 1 to 5, in which the outer edges of the upper segments 2c1, 2c2 of the haptic loops 2' are formed with ridges 7. This arrangement permits a better engagement of this part of the haptic loops with an internal periphery of the ciliary sulcus 102 and, as such, a better fixation of the IOL 20.

Figure 9:
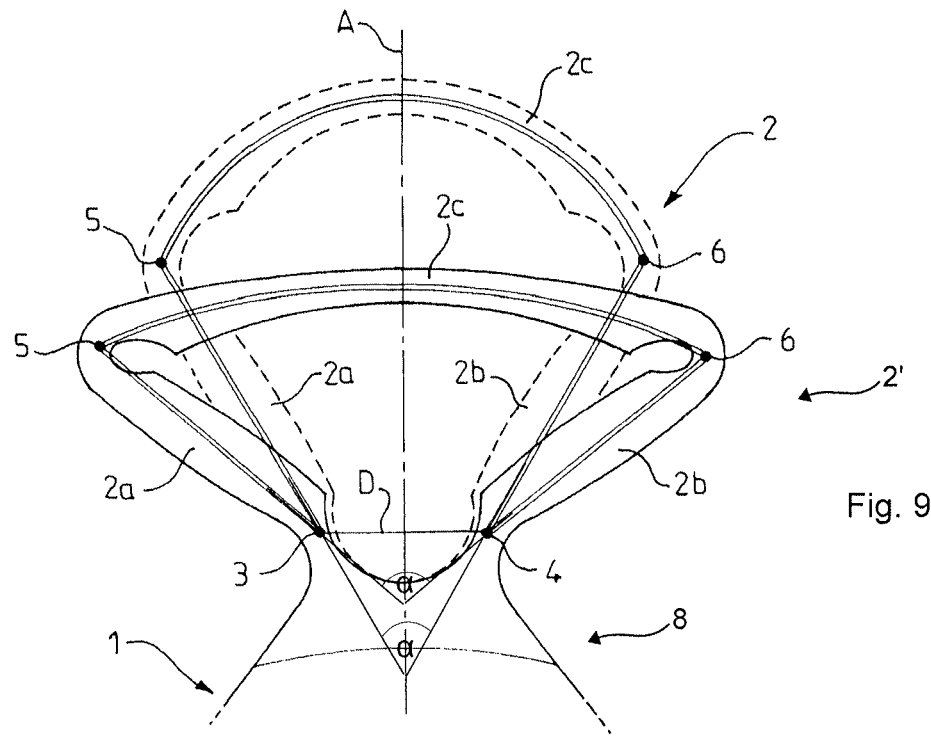
FIG. 9 is a schematic perspective view of the IOL according to FIG. 1 arranged in a proximal position in front of a primary IOL.
Figure 8:
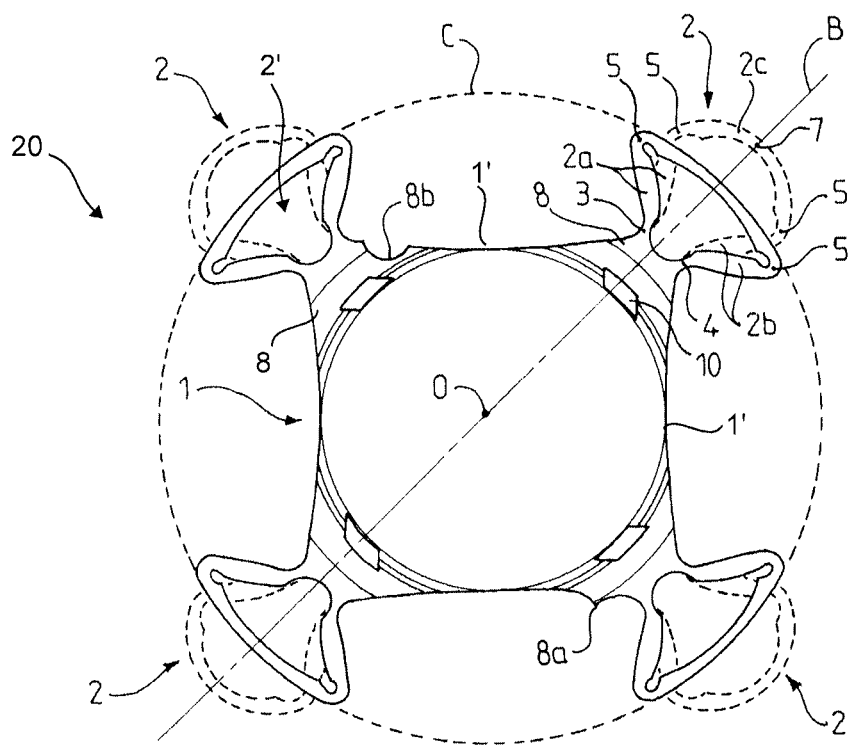
FIG. 8 is a schematic back view of another preferred embodiment of a IOL according to the invention.

FIGS. 8 and 9 show a schematic view of a further embodiment of a IOL 20 according to the invention, having a different haptic loop 2 design than the previously described embodiments. The haptic loops 2 are illustrated at rest (broken lines) and in the state of maximum deformation (solid lines). In contrast to the embodiment shown in FIGS. 1 and 2, the upper segment 2c of the haptic loop 2 according to the present embodiment is formed as a single arched segment 2c without any flexion points separating it. All the other features of the IOL 20 are similar and are designated by the same reference numerals. The upper segment 2c is elastic and arched such that, under the effect of the compression forces acting in the direction of the optically active lens part 1, the pivoting of the lower segments 2a, 2b in a plane perpendicular to the optical axis O produces the lowering of the upper flexion points 5, 6 and the flattening of the elastic upper segment 2c. According to the present embodiment elastic deformation of the loops 2' occurs not only at the flexion points 3, 4, 5, 6 but also in the upper segment 2c. As in the embodiment depicted in FIGS. 4 and 5, the haptic loop 2' cannot continue to deform beyond the lower position indicated in FIGS. 8 and 9 with solid lines.

The elastic flexion points 3, 4, 5, 6, 7 allow for the elastic deformation of the loops 2', other portions of the loop 2' are preferably more ridged in order to ensure that upon compression any flexion of the loops 2' occurs at the flexion points 3, 4, 5, 6, 7.

Similarly to the preceding embodiments, this is also an additional IOL 20 for positioning in the ciliary sulcus 102 in front of a capsular bag IOL 30. It can likewise be made with a ridged contour on the outer edge of the upper segments 2c via which the haptic loops 2' abut the internal periphery of the ciliary sulcus 102.

FIG. 10 illustrates the position of the secondary IOL 20 and the primary IOL 30 within a patient's eye 100. The secondary IOL 20 has been surgically implanted in the ciliary sulcus 102 of the pseudophakic eye 100, i.e. in addition to a primary IOL 30 that has already been implanted in the capsular bag 107 of the posterior chamber 104 of the patient's eye 100 prior to the implantation of the secondary IOL 20. The haptics 2 fix and stabilize the secondary IOL 20 within the ciliary sulcus 102 of the patient's eye 100. The optically active lens part 1 of the secondary IOL 20 is designed to project an image through the primary IOL 30 onto a retina 108 of the 100. FIG. 10 illustrates how light rays 120 coming from a source at a distance d from the eye 100 are focused onto a macula 109 of the retina 108 when the pupil 105 is constricted. The secondary IOL 20 is arranged optically coaxial to the primary IOL 30, for focusing a combined image on the retina 108, e.g. for additionally magnifying at least a central part of the image of the primary IOL 30 projected onto the macula 109 of the retina 108. According to this embodiment, the secondary IOL 20 improves the visual capabilities of the patient by additionally magnifying at least a central part of the image of the primary IOL 30.

The secondary IOL 20 may be designed to fulfill other purposes such as correcting of residual or resulting deficiencies after the implantation of the primary IOL 30 in the capsular bag 107, or adding new features to the optical system of the eye 100, for example correction of corneal astigmatism, modification of near sight by means of multifocal lenses, fitting of a filter for blue light in cases of sensitivity to light.

The IOL 20 according to the invention may be used alone as well, e.g. when the capsular bag 107 is unable to receive a corrective lens.

Various modifications to the above disclosed embodiments will be apparent to a person skilled in the art without departing from the scope of protection determined by the attached claims.

The invention claimed is:

1. A foldable intraocular lens, made from a foldable soft material, for implantation in a ciliary sulcus of an eye having an iris, comprising:
    an optically active lens part having an optical axis and at least four coplanar haptics unitary with the optically active lens part and uniformly spaced about a periphery of the optically active lens part, each haptic consisting of a closed haptic loop and single flat triangular shoulder;
    the optically active lens part having a non-convex rim between any two neighboring haptics being free from surface irregularities that interfere with the iris;
    each rim and triangular shoulders being formed such that an orthogonal projection of the IOL on to a plane perpendicular to the optical axis of the optically active lens part is substantially a concave or straight line between any two neighboring haptic loops as viewed from the optical axis:
    the single flat triangular shoulder of each haptic connecting the loop with the optically active lens part and spacing the loop from the optically active lens part, the haptic loops being elastically deformable in a plane perpendicular to the optical axis of the optically active lens part in a direction toward the optically active lens part, and the flat triangular shoulder having a decreasing cross-section and width toward an adjacent haptic loop.

2. The foldable intraocular lens according to claim 1, wherein each haptic loop comprises an elongated arched upper segment with opposed end portions and a pair of lower segments, each lower segment pivotably joined to the upper segment at one of said end portions of the upper segment and pivotably joined to the shoulder at a distance therebetween, such that said lower segments converge in the direction of the optically active lens part and a length of each upper segment is less than a sum of lengths of said lower segments and said distance.

3. The foldable intraocular lens according to claim 2, wherein the lower segments of each loop lie at an angle not exceeding 100 degrees in an undeformed state of said loop and opening in a direction of the upper segment.

4. The foldable intraocular lens according to claim 2, wherein each lower segment is joined to the upper segment at one of said end portions of the upper segment at first flexion points, which are configured so as to make it possible for the arched upper segment and the two lower segments of each loop to pivot relative to each other about said first flexion points in said plane that is perpendicular to the optical axis of the optically active lens part, and each lower segment is joined to the shoulder at the second flexion points, which are configured so as to make it possible for the two lower segments of each loop to pivot relative to the optically active lens part of the lens about said second flexion points in said plane that is perpendicular to the optical axis.

5. The foldable intraocular lens according to claim 2, wherein each lower segment is joined to the upper segment at one of said end portions of the upper segment at first flexion points and to the shoulder at second flexion points, the two lower segments and the upper segment of each loop are configured to occupy a non-deformed state in which the lower segments are lying at a first angle to each other and the first flexion points are at a first distance from each other, and an elastically deformed state in which the arched upper segment flattens, the lower segments are lying at a second angle to each other and the first flexion points are at a second distance from each other, the second angle being greater than the first angle and the second distance being greater than the first distance.

6. The foldable intraocular lens according to claim 2, wherein the arched upper segment in each closed loop is formed by at least two portions connected to each other by a third flexion point.

7. The foldable intraocular lens according to claim 2, wherein in a state of maximum compression of the closed loops, the intraocular lens has an overall diameter between 10.5 mm and 12.5 mm.

8. The foldable intraocular lens according to claim 2, wherein each lower segment is joined to the upper segment at one of said end portions of the upper segment at first flexion points and to the shoulder at second flexion points, and a cross-section of each loop at the first and second flexion points of said loop is smaller than a cross-section of the lower segments and the upper segments.

9. The foldable intraocular lens according to claim 2, wherein the shoulders have projections or recesses for performing a positioning function.

10. The foldable intraocular lens according to claim 2, wherein a posterior face of the optically active lens part is provided with spacing projections.

11. The foldable intraocular lens according to claim 2, wherein a posterior face of the optically active lens part has recesses that are centered on diameters passing through poles of two opposing loops.

12. The foldable intraocular lens according to claim 2, wherein an outer edge of the upper segment of each loop is ridged.

13. The foldable intraocular lens according to claim 2, wherein an outer edge of the lower segments of each loop is straight.

14. The foldable intraocular lens according to claim 1, wherein the foldable intraocular lens is formed as a unitary single-piece intraocular lens.

15. The foldable intraocular lens according to claim 1, wherein the optically active lens part is at least partially toric.

16. The foldable intraocular lens according to claim 1, wherein the rim of the optically active lens part is free from surface irregularities having a radius greater than 0.6 mm.

17. The foldable intraocular lens according to claim 1, wherein the rim of the optically active lens part is free from surface irregularities having a radius greater than 0.3 mm.

\* \* \* \* \*